United States Patent [19]
Phillips

[11] 4,080,965
[45] Mar. 28, 1978

[54] IN-LINE CANNULA VALVE ASSEMBLY

[75] Inventor: Thomas E. Phillips, Ingleside, Ill.

[73] Assignee: Baxter Travenol Laboratories, Inc., Deerfield, Ill.

[21] Appl. No.: 728,479

[22] Filed: Sep. 30, 1976

[51] Int. Cl.² .................................................. A61M 5/14
[52] U.S. Cl. .............................. 128/214 D; 128/214.2; 128/247; 137/68 R; 251/342
[58] Field of Search .............. 251/342, 347, 348, 353; 222/81, 83, 402.24; 128/214 R, 214 C, 214 D, 214.2, 247

[56] References Cited

U.S. PATENT DOCUMENTS

| | | | |
|---|---|---|---|
| 2,552,155 | 5/1951 | Danielson | 222/81 |
| 3,613,728 | 10/1971 | Steiman | 251/353 |
| 3,685,795 | 8/1972 | Caster | 251/342 |
| 3,707,972 | 1/1973 | Villari et al. | 251/342 X |

FOREIGN PATENT DOCUMENTS

| | | | |
|---|---|---|---|
| 1,528,025 | 4/1968 | France | 128/214 D |
| 1,020,654 | 9/1964 | United Kingdom | 137/318 |

Primary Examiner—Martin P. Schwadron
Assistant Examiner—Richard Gerard
Attorney, Agent, or Firm—Paul C. Flattery; John P. Kirby, Jr.; Garrettson Ellis

[57] ABSTRACT

An in-line cannula valve assembly for controlling flow through a conduit, comprising a housing, including a collapsible housing part having a flexible wall, joined to a relatively rigid housing part. A first fluid passage in the relatively rigid housing part are provided as a portion of the conduit. A cannula element is positioned with its piercing point end in the second fluid passage, and the opposite end is positioned adjacent the first fluid passage. The cannula element is adapted for longitudinal movement through the first and second passages. A longitudinal groove is defined in the cannula element extending to the opposite end, but terminating short of the piercing point end. Sealing means are positioned about the cannula element. Thus, the cannula element may be positioned in either a first, closed position in which the longitudinal groove is spaced from the sealing means, or a second, flow-permitting position in which the groove passes through the sealing means, to permit fluid flow along the groove through the sealing means. A rupturable membrane is also provided to prevent flow through the conduit, being positioned to be ruptured by the piercing point of the cannula element by longitudinal movement thereof.

10 Claims, 6 Drawing Figures

U.S. Patent  March 28, 1978  4,080,965
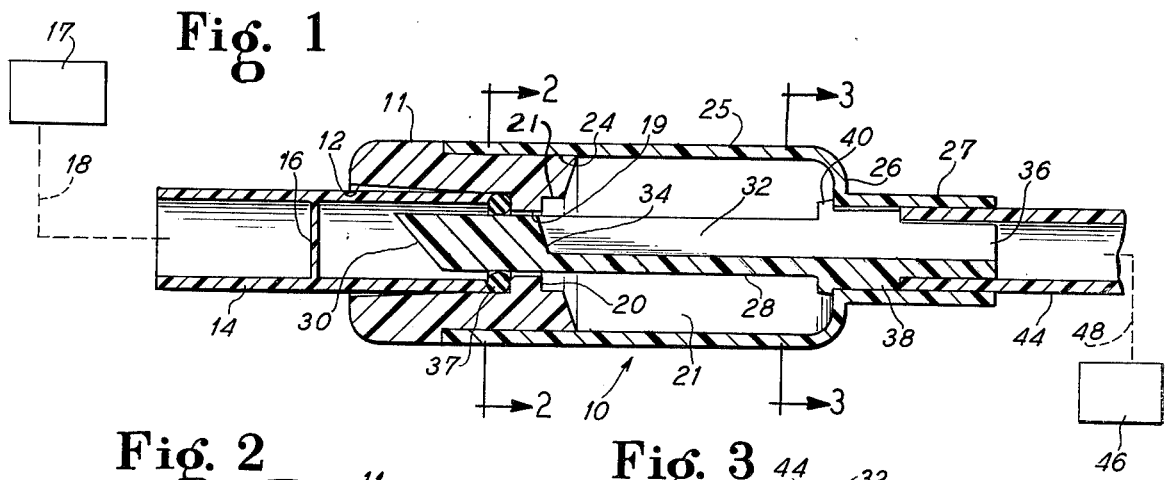
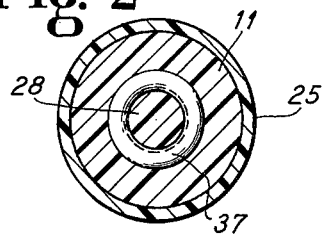
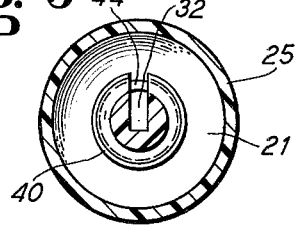
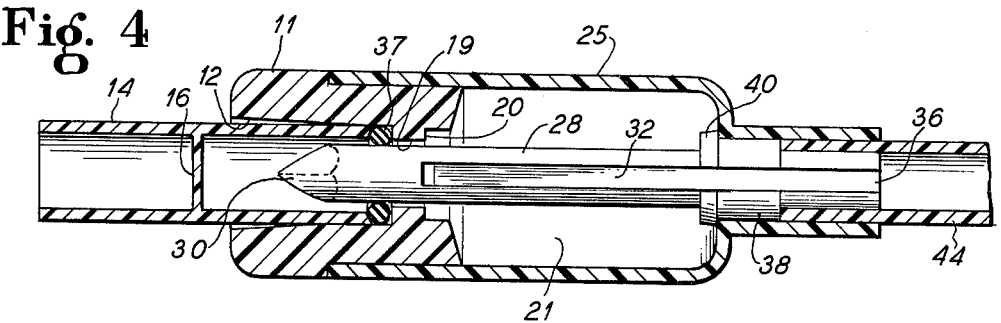
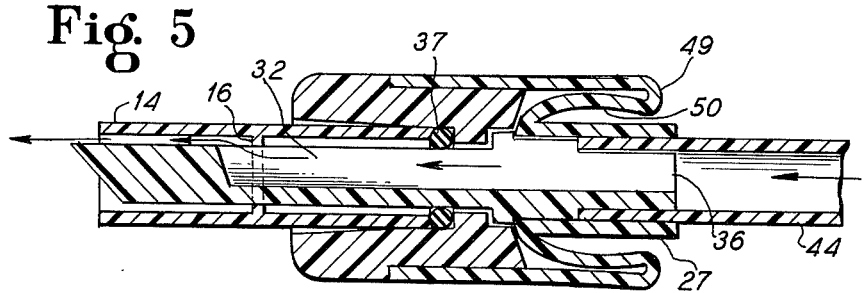
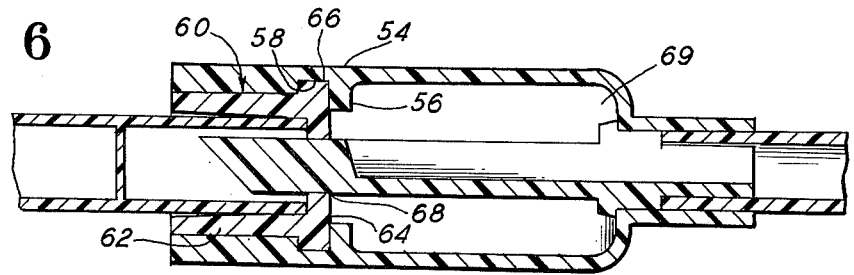

IN-LINE CANNULA VALVE ASSEMBLY

BACKGROUND OF THE INVENTION

Blood bags and the like which are interconnected in sterile manner are used for the collection and processing of blood under sterile conditions.

A valve is generally used to initially open the connection in the conduit between the two containers, being equipped with means for reclosing of the valve and reopening it again as desired.

In U.S. Pat. No. 3,685,795 a cannula valve is disclosed causing a spike for puncturing a diaphragm to open the flow path, and also providing other valving means for reclosing the path again, as desired.

However, this structure must be collapsed to rupture the diaphragm, and then must be re-extended again to reopen the flow path. Also the components of the device are rather expensive and difficult to assemble.

The structure of this invention exhibits a novel valve system utilizing a grooved cannula member rather than a hollow structure, as has been commonly used in the prior art. The grooved cannula is considerably less expensive than hollow structures, and also is more easily inspected for defects and the like, prior to assembly, than a tubular cannula.

The device of this invention also provides an open valve immediately after penetration of the diaphragm, without withdrawing, while still permitting resealing of the valve.

Thus, the valve of this invention with its selectively openable flow path, may be used in apparatus to store and process separate medical fluids or other fluids which have a short shelf life, or a high level of incompatability when mixed.

DESCRIPTION OF THE INVENTION

In accordance with this invention, an improved in-line cannula assembly is provided for controlling flow through a conduit, particularly under sterile conditions. The cannula valve assembly includes a housing which has a collapsible housing part comprising a flexible wall, joined to a relatively rigid housing part, compared with the collapsible housing part. A first fluid passage is provided in the collapsible housing part communicating with the conduit, and a corresponding second fluid passage is provided in the relatively rigid housing part in communication with the first fluid passage and the remainder of the conduit.

A cannula element is provided defining a piercing point at one end thereof. The piercing point end is positioned in the second fluid passage of the rigid housing part, while the opposite end of the cannula is positioned in the first fluid passage.

The cannula element is adapted for longitudinal movement through the first and second fluid passages. A longitudinal groove is defined in the cannula element extending to said opposite end thereof, but terminating short of the piercing point.

Sealing means are positioned about the cannula element so that longitudinal movement of the cannula element permits the positioning of the cannula element in a first, closed position in which the longitudinal groove is spaced from the sealing means, and, alternatively, a second, flow-permitting position in which the groove passes through the sealing means to permit fluid flow along the groove through the sealing means. A rupturable membrane is provided to prevent flow through the conduit. The membrane is positioned to be ruptured by the piercing point of the cannula element by longitudinal movement thereof.

Accordingly, the cannula valve of this invention may be initially sealed by the rupturable membrane. Thereafter, the cannula valve may be collapsed to pierce the rupturable membrane to open the device since in that position the groove may pass through the sealing means. Thereafter, withdrawing of the cannula valve, so that the groove no longer passes through the sealing means, results in the closing of the valve to fluid flow.

In the drawings:

FIG. 1 is a longitudinal sectional view of the in-line cannula assembly, with other parts indicated schematically.

FIG. 2 is a sectional view taken along line 2—2 of FIG. 1.

FIG. 3 is a sectional view taken along line 3—3 of FIG. 1.

FIG. 4 is a sectional side view of the in-line cannula assembly shown in FIG. 1, but rotated 90° therefrom, with the housed cannula element shown in elevation.

FIG. 5 is a longitudinal sectional view similar to that of FIG. 1, but showing the cannula element advanced into a position to penetrate the rupturable membrane and with the collapsible housing portion shown in collapsed position.

FIG. 6 is a longitudinal sectional view of an alternative embodiment of the cannula valve of this invention.

Referring to FIGS. 1 through 5, housing 10 includes the relatively rigid housing part 11 which defines a fluid passage 12. Mounted in the fluid passage is a substantially rigid tubular member 14, having a rupturable membrane 16 occluding the bore of the tubular member. A fluid receptacle such as blood bag 17 is connected by conduit 18 to tubular member 14 on one side of membrane 16.

Fluid passage 12 in the relatively rigid part 11 communicates with a reduced-diameter communicating passage 19 (FIG. 4) defined by annular flange 20.

Housing 10 also defines collapsible housing part 25, which comprises a flexible tubular wall as shown. Annular seat 24 on relatively rigid housing part 11 tightly engages the open end of collapsible housing part 25, which may be tightly mounted to the seat by using an elastic band or appropriate adhesive heat seal or the like. Collapsible housing part 25 may be made of polyvinylchloride plastic or other flexible material as desired.

Housing parts 11 and 25 may also be made out of a single piece, if desired, relying upon the greater thickness of part 11 to obtain its relative rigidity.

Collapsible housing part 25 narrows down at its outer end 26 to form a tubular stub or terminus 27.

Collapsible housing part 25 is shown to be hollow, thus defining a fluid passage 21 through it, as part of the conduit in which the cannula valve assembly is carried.

Cannula element 28 is located within housing 10. Cannula element 28 defines a forwarding piercing end 30, shown positioned in the fluid passage of housing part 11 and the bore of tubular member 14, and spaced from rupturable membrane 16 in the initial position, as illustrated in FIG. 1. The opposite end 36 of cannula element 28 is positioned adjacent the fluid passage of collapsible housing part 25, being firmly carried by stub 27, so that the manual manipulation of stub 27 permits the longitudinal movement of cannula 28.

Cannula 28 is provided with a longitudinal groove 32, which extends from a forward end 34 spaced from piercing end 30, to a fluid opening at opposite end 36. Groove 32 normally extends the entire length of fluid passage 21 of collapsible housing part 25. Cannula 28 may be substantially cylindrical as shown.

A sealing means such as O-ring seal 37 is positioned in fluid passage 12 to sealingly engage the cylindrical body of the cannula 28.

As shown in the initial position of FIG. 1, cannula 28 is positioned so that longitudinal groove 32 is completely positioned on one side of and spaced from O-ring seal 37. Thus, the fluid path between the fluid source 17 and flow path 21 of collapsible housing part 25 is sealed by O-ring 37.

To open the cannula assembly of this invention, cannula member 28 is advanced by collapsing housing part 25 as shown in FIG. 5, so that piercing end 30 penetrates rupturable membrane 16. Simultaneously, cannula member 28 is advanced so that groove 32 passes through O-ring 37, providing a flow path through the seal provided by O-ring 37. Groove 32 can also extend beyond ruptured membrane 16, if desired, to reduce flow blockage by the membrane fragments.

Thereafter, if the flow path is desired to be sealed again, cannula 28 may be withdrawn to its first position again, as shown in FIG. 1. In this position, the sterile seal is once again re-established by O-ring seal 37, since groove 32 no longer passes through it.

The rear end of cannula 28 may be provided with an enlarged portion 38 to closely fit tubular terminus 27. Enlarged portion 38 keeps cannula member 28 from passing too far into tube 44.

Flange 40 can form a taper lock fit with enlarged diameter 21 in housing part 11, to hold the cannula member in open position until positively closed by deliberate withdrawing action.

The portion of cannula 28 behind enlargement 38 may be relatively thin, to be spaced from the interior wall of the tubular terminus 27. A portion of tubular member 44 may be inserted into the resulting space as shown, as a connection means.

The tubular member 44 may be connected to another fluid receptacle or source 46 by means of a conduit line 48 which is connected to or integral with tubular member 44.

In use, the collapsible housing part 25 is collapsed when the cannula element is pushed to an advanced position, as shown in FIG. 5. A fold 49 of the collapsed portion is shown.

The alternative embodiment of FIG. 6 shows a modified housing providing a mechanical interlock between housing parts. Collapsible housing part 54 of this embodiment is provided with a continuous interior lip 56, which may be of annular configuration. Continuous inner lip 56 may be relatively soft, to serve as a seal. The collapsible housing part is also provided with a continuous inner groove 58, which also may have an annular configuration.

A substantially rigid housing part 60 is mechanically interlocked to the open end of collapsible housing part 54. Substantially rigid housing part 60 operates as an insert defining tubular wall 62, having a configuration matching the supported portion of collapsible housing part 54. Tubular wall 62 is joined to head portion 64, defining a continuously extending shoulder 66, which resides in groove 58 in collapsible housing 54. Head portion 64 also abuts against lip 56 when so seated, to effect a sealing mechanical interlock.

A central opening 68 is defined to receive the elongated cannula element, which is of a design and function similar to that of FIGS. 1 through 5. Head portion 64 serves as the sealing means, analogous to O-ring 37, in this embodiment.

The above has been offered for illustrative purposes only, and is not for the purpose of limiting the invention of this application, which is as described in the claims below.

That which is claimed is:

1. An in-line cannula valve assembly for controlling flow through a conduit, comprising: a housing, including a collapsible housing part comprising a flexible wall, joined to a relatively rigid housing part; a first fluid passage in said collapsible housing part, and a second fluid passage in said relatively rigid housing part; a cannula element, defining a piercing point at a first end of the cannula element, the piercing point end being positioned in said second fluid passage, and the opposite end of the cannula being positioned adjacent said first fluid passage, said cannula element being adapted for longitudinal movement through said first and second fluid passages; a longitudinal groove defined in the cannula element extending to said opposite end thereof and terminating short of said piercing point to define a sealing surface between said piercing point and groove; sealing means positioned about said cannula element, whereby longitudinal movement of said cannula element permits the positioning of said cannula element in a first, closed position, in which said longitudinal groove is spaced from said sealing means and the sealing means engages the sealing surface, and a second, flow-permitting, longitudinal position in which said groove passes through said sealing means to permit fluid flow along said groove between said first and second fluid passages; and a rupturable membrane preventing flow through said conduit, and positioned to be ruptured by the piercing point of said cannula element by longitudinal movement thereof.

2. The in-line cannula assembly of claim 1 in which said relatively rigid housing part includes a reduced-diameter passage as part of said conduit, defined by an annular flange, said cannula element being positioned for passage through said reduced-diameter passage.

3. The in-line cannula assembly of claim 2 in which said collapsible housing part defines a reduced-sized tubular terminus at the end of said collapsible housing part which is remote from said rupturable membrane, said opposite end of the cannula being carried in said tubular terminus.

4. The in-line cannula assembly of claim 2 as part of a multiple blood bag system, said cannula valve assembly being positioned in a flow conduit between two blood bags.

5. The in-line cannula of claim 2 in which said sealing means comprises an O-ring positioned adjacent said annular flange.

6. The in-line cannula of claim 2 having mechanical interlock means for connecting said rigid and collapsible housing parts.

7. An in-line cannula valve assembly for controlling flow through a conduit, comprising: a housing, including a collapsible housing part comprising a flexible wall, joined to a relatively rigid housing part; a first fluid passage in said collapsible housing part, and a second fluid passage in said relatively rigid housing part; a cannula element adapted for longitudinal movement through said first and second fluid passages; a longitudinal groove defined in the cannula element extending from one end of the cannula element to a point spaced from the other end thereof, a portion of said cannula element adjacent said other end defining a solid, unbroken outer surface: and sealing means, associated with said cannula element, to prevent fluid flow through said first and second fluid passages while said cannula element occupies a first longitudinal position, while fluid flow is permitted through said first and second fluid passages and through said groove when the cannula element occupies a second longitudinal position.

8. The in-line cannula valve assembly of claim 7 in which said sealing means associated with the cannula element is positioned in said housing adjacent said cannula element, whereby said cannula element is movable with respect thereto.

9. The in-line cannula valve assembly of claim 8 in which said relatively rigid housing part includes a reduced-diameter passage as part of said conduit, said cannula element being positioned for passage through said reduced-diameter passage, and said sealing means comprises an O-ring positioned adjacent said reduced-diameter passage.

10. The in-line cannula valve assembly of claim 9 in which a rupturable membrane is positioned across the flow path through said conduit, in a position to be ruptured by said cannula element by longitudinal movement thereof, for initial opening of the valve.

* * * * *